United States Patent [19]
Langer, Jr. et al.

[11] 3,933,879
[45] *Jan. 20, 1976

[54] CHELATED LITHIUM ALUMINUM COMPOUNDS

[75] Inventors: Arthur W. Langer, Jr., Watchung; Thomas A. Whitney, Roselle, both of N.J.

[73] Assignee: Exxon Research and Engineering Company, Linden, N.J.

[ * ] Notice: The portion of the term of this patent subsequent to May 22, 1990, has been disclaimed.

[22] Filed: Mar. 23, 1973

[21] Appl. No.: 344,230

Related U.S. Application Data

[63] Continuation-in-part of Ser. No. 808,328, March 18, 1969, Pat. No. 3,734,963.

[52] U.S. Cl......... 260/448 R; 252/49.7; 260/239 E; 260/247; 260/268 R; 260/290; 260/293; 260/349; 260/429 J; 260/429.1; 260/429.5; 260/429.7; 260/430; 260/431; 260/439 R; 260/440; 260/448 A; 260/570.5 P; 260/577; 260/583 R; 260/583 D; 260/583 P; 260/584 C; 260/606.5 P; 260/607 A; 260/609 R; 260/609 E; 260/638 B; 260/651 HA

[51] Int. Cl.² ........................................... C07F 5/06

[58] Field of Search........ 260/448 R, 448 B, 448 A, 260/448 AD

[56] References Cited
UNITED STATES PATENTS 3,200,106  8/1965  Dickson ........................ 260/448 B
3,734,963  5/1973  Langer et al.................... 260/448 X

*Primary Examiner*—Helen M. S. Sneed
*Attorney, Agent, or Firm*—John P. Corcoran; Joseph J. Allocca

[57] ABSTRACT

Chelated lithium aluminum compounds are prepared by mixing a lithium aluminum compound such as a lithium aluminum hydride with a chelating agent wherein the agent contains at least one nitrogen atom. The chelating agent is a tertiary polyamine or aminoether. The resultant chelate is used for a variety of processes such as separations, catalytic reactions, substitution reactions, reductions, electrochemical reactions, and also as an oil and fuel additive.

8 Claims, No Drawings

CHELATED LITHIUM ALUMINUM COMPOUNDS

This application is a continuation-in-part of an application bearing Serial No. 808,328 filed March 18, 1969.

THE PRIOR ART

It is well known (e.g. see British Pat. No. 1,051,269) that organolithiums such as n-butyllithium will form chelate complexes with certain bifunctional Lewis bases, particularly di-tertiary amines such as tetramethylethanediamine. According to this patent, the complexes are prepared by mixing the organolithium and the di-tertiary diamine, generally in the presence of a hydrocarbon solvent or excess amounts of the diamine. The chelate complex forms quite rapidly since the organolithium and the diamine form a homogeneous solution (in a hydrocarbon or excess diamine) and the chelate complex may then be isolated by removal of the diluent.

It is also well known (e.g. see British Pat. No. 1,031,179) that alkali metals such as sodium or lithium in finely divided form can be reacted with certain organic compounds to produce the corresponding organo alkali metal salts, providing the reaction is carried out in the presence of certain amines in which at least one of the amino groups is a primary or secondary amino group. Thus, a lithium dispersion (in heptane) can upon admixture with ethylene diamine, yield N-lithio-ethylene diamine; this latter matter upon treatment with acetylene will yield monolithium acetylide ethylene diamine.

It is also well known (U.S. Pat. No. 2,726,133) that lithium chloride may be extracted from crude aqueous lithium chloride with the aid of an inert solvent of 3 to 8 carbon atoms containing at least one nitrogen or oxygen atom such as the alkanols, corresponding ketones and aldehydes, pyridine and quinoline.

Bedell in his U.S. Pat. No. 3,258,490, teaches the use of primary amines to prepare insoluble high melting compounds of lithium perchlorate. Despite Bedell's reference to "chelation," it is apparent from the properties of his complexes that they are not chelates but are open chain polymeric complexes. Bedell does not show, suggest or teach that tertiary diamines are capable of forming similar complexes or that they are in any way equivalent to primary diamines.

THE PRESENT INVENTION

This application is a continuation-in-part of Ser. No. 808,328 filed Mar. 18, 1969 entitled "Inorganic Lithium Amine Complexes." It has now been unexpectedly discovered that a complex of certain inorganic lithium salts and certain complexing agents can be readily prepared. This is highly surprising for the various reasons set forth immediately below.

At the outset, it was surprising that a complex of an inorganic lithium salt could be prepared since the general chemistry (i.e. properties, reactivity, etc.) of inorganic lithium salts differ drastically from that of organolithium compounds or lithium metal. Many organolithium compounds are generally soluble in hydrocarbons and thus readily form complexes upon admixture with certain complexing agents. However, inorganic lithium salts are generally insoluble in hydrocarbons; thus, it was wholly unexpected to find that when many inorganic lithium salts were mixed with a hydrocarbon containing the complexing agent, the inorganic lithium salts dissolved in the reaction medium and stable complexes of the chelating agent with the lithium salt could be obtained from the reaction mixture.

It is well known that one of the significant factors used in predicting whether a reaction can be accomplished with a given material is whether the lattice energy of such material is low enough to be overcome by the other reactant so as to form a new compound. Thus, it was highly surprising to find that the inorganic lithium salts which have significantly higher lattice energies than those of organolithium compounds, nevertheless can form complexes with the same type (and indeed many more types) of complexing agent as those used in conjunction with the organolithium compounds.

THE LITHIUM COMPOUND

The first component of the novel chelated lithium compounds of this invention is a lithium compound having a lattice energy no greater than about that of lithium hydride, preferably no greater than about 210 kilocalories per mole (measured at about 18°C). The lattice energies of various inorganic lithium salts may be found in the "Handbook of Electrochemical Constants" by Roger Parsons (Academic Press 1959).

The lithium compounds useful for this invention must have less than the requisite maximum lattice energy and they will normally have melting points less than about 650°C. The lithium compounds for the purposes of this invention, have no hydrocarbon radical bonded directly to the lithium atom and any hydrocarbon radical present in the anion moiety must be indirectly bonded to the lithium through a third atom which cannot be nitrogen, oxygen, phosphorus or sulfur. Thus, lithium compounds such as n-butyllithium and phenyllithium are outside the scope of this invention. Similarly, compounds of the type LiOR, LiNHR or LiNR$_2$, LiPR$_2$, LiOOCR are outside the scope of this invention. On the other hand, compounds of the type LiCN, LiSCN, LiAlR$_2$Cl$_2$, LiAlH(OR)$_3$, LiBH(OR$_3$), LiAlR$_3$H are within the scope of this invention.

Specific nonlimiting examples of useful inorganic lithium salts are those in which the anion is: azide, chlorate, cyanide, fluosulfonate, chloride, bromide, iodide, iodate, nitrate, hypochlorite, nitrite, thiocyanate, perchlorate, Br$_3$, I$_3$, ClBr$_2$, IBr$_2$, ICl$_4$, BrF$_4$, IF$_6$.

Also useful are those lithium compounds in which the anion is a complex metal anion which may be represented by th formula R"$_n$MX$_m$ wherein n is an integer of 0 to 6 inclusive depending on the valence of M, m is an integer and (n + m − 1) equals the valence of M. X is a halogen, R" is a C$_1$-C$_{20}$ alkyl, aryl or aralkyl radical and M is a metal selected from the group consisting of beryllium; magnesium; Group Ib elements; Group IIb elements; Group III elements, Group IVa elements other than carbon and silicon; Group Va elements other than nitrogen; and the transition metals, i.e. subgroup b of Groups IV through VIII. The Periodic Table employed in describing this invention is that which appears on the back cover of "Handbook of Chemistry and Physics" (Chemical Rubber Co., 49th Edition).

Nonlimiting examples of useful complex metal anions include the hydridoaluminates, the hydridoborates, the chloroaluminates (tetra-, hepta-, etc.), the aluminum alkyl halides, AuBr$_4$, BF$_4$, BeCl$_4$, SnCl$_6$, PF$_6$, TiCl$_6$, FeCl$_4$, Cr(CO)$_5$I, MnCl$_3$, Ni(CN)$_4$, VF$_6$, HgCl$_3$, B$_2$H$_7$, UF$_4$, AsF$_6$.

Preferably, the lithium compound is one of the following: lithium chloride, lithium bromide, lithium iodide, lithium aluminum hydride, lithium borohydride, lithium nitrate, lithium hexafluorophosphate, lithium tetrafluoborate, lithium tetraphenylborate, $LiAl(C_2H_5)H_3$, $LiAl(C_2H_5)_2H_2$, $LiAl(C_2H_5)_3H$, $LiAl(C_2H_5)_4$, lithium perchlorate, lithium azide, $LiAsF_6$ and $Li_2BeF_4$. More preferably, the lithium compound of the subject invention is selected from the group consisting of $LiAlR_nX_{(4-n)}$ and $LiAlR_mX'_{(4-m)}$ wherein R is a hydrogen or a $C_1$-$C_{20}$ hydrocarbyl group, X is selected from the group consisting of chlorine, bromine, iodine; X' is selected from the group consisting of $C_1$-$C_{20}$ alkoxide, $C_1$-$C_{20}$ thioalkoxide, $C_2$-$C_{40}$ hydrocarbyl secondary amides and $C_2$-$C_{40}$ hydrocarbyl secondary phosphides; n is an integer from 0 to 4, and m is an integer from 1 to 4. Typical examples are $LiAlH_3Cl$, $LiAlR_3Cl$, $LiAlR_3Br$, $LiAlR_3I$, $LiAlR_3NR_2$, $LiAlR_2(NR_2)_2$, $LiAlH_2(NR_2)_2$, $LiAlH_2ORNR_2$, $LiAlH_2BrOR$, $LiAlH_2BrNR_2$, $LiAlHBrORNR_2$, $LiAlH_3SR$ and $LiALH_2NR_2SR$.

Specific nonlimiting examples of the lithium compounds of this invention are $LiAlH[N(C_2H_5)_2]_3$, $LiAlH_2[N(C_3H_7)_2]_2$, $LiAlH_3N(C_{10}H_{21})_2$, $LiAlH_3OC_2H_5$, $LiAlCl(C_4H_9)_3$, $LiAlBr(C_4H_9)_3$, $LiAl(C_4H_9)_3$, $LiAlH_2BrC_4H_9$, $LiAlH_2N(C_{10}H_{21})_2OC_2H_5$, $LiAlH_3N(C_6H_{11})_2$, $LiAlHBr(i-C_4H_9)_2$, $LiAlH_2N(C_2H_5)_2SC_6H_5$, $LiAl(C_2H_5)_2N(C_2H_5)_2Br$, $LiAl(C_6H_5)_3Br$, $LiAlCl_2BrC_2H_5$, $LiAlH_3SC_8H_{17}$, $LiAlHBrOC_2H_5N(C_{10}H_{21})_2$, $LiAlH_2ISCH_3$, $LiAl(C_2H_5)_2C_{20}H_{41}Br$, $LiAlH_3OC_6H_5$, $LiAlH_3SC_{20}H_{41}$, $LiAlH_3OC_{20}H_{41}$, $LiAlH_3P(C_6H_{11})_2$ and the like.

Most preferred are the lithium compounds having the above formulas wherein R is a hydrogen atom, n is an integer from 1 to 4, and m is an integer from 1 to 4. Illustrative examples include $LiAlH_4$, $LiAlH_3Cl$, $LiAlH_2Br_2$, $LiAlH_3O$-menthyl*, $LiAlH_3N(C_2H_5)_2$, $LiAlH_2Br(SC_6H_5)$, $LiAlH_2[OCH*(CH_3)C_6H_5]_2$, $LiAlH_3NHCH*(CH_3)C_6H_5$, $LiAlH_3O$ $LiAlH_3OC*(C_6H_5)(CH_2C_6H_5)*CH(CH_3)N(CH_3)_2$, wherein * denotes optical activity, and the like.

THE CHELATING AGENT

The chelating agent is a polyfunctional Lewis base which contains at least two functionalities: at least one functionality is a tertiary amine group; at least one other functionality is a tertiary amine group or an ether group.

The chelating agent has one required functionality in a spatial relationship with the other required functionality(ies) in the molecules such that co-ordinate bonds are established between the functionalities and the lithium cation of the lithium compound.

The chelating agent may be sparteine, an $N,N'$-di($C_1$-$C_4$ alkyl) bispidin, tris-($\beta$-$C_1$-$C_4$-dialkylaminoethyl)amine as well as those compounds falling within the scope of the following general formulas:

I. 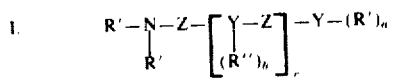

II. 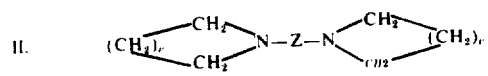

wherein a is 1 or 2, depending on the valence of Y; b is 0 or 1, depending on the valence of Y; c is an integer of 0 to 4, inclusive; e is an integer of 0 to 3, inclusive; R' is the same or different $C_1$-$C_4$ alkyl radical; R'' is the same or different $C_1$-$C_4$ alkyl radical or $C_6$-$C_{10}$ aryl or aralkyl radical; Y is a nitrogen or oxygen atom; and Z is a nonreactive radical selected from the group consisting of (1) $C_4$-$C_{10}$ cycloaliphatic or aromatic radicals and their lower alkyl derivatives wherein said radicals are attached to the nitrogen and Y atoms in Formula I and the nitrogen atoms in Formula II at 1,2-positions on the aromatic rings or 1,2- or 1,3-positions on the cycloaliphatic rings; and (2) 1 to 4 methylenic radicals, wherein each methylenic radical contains 0 to 2 monovalent hydrocarbon radicals of 1 to 6 carbon atoms.

Suitable nonlimiting examples of chelating Lewis bases falling within the scope of the above formulas are:

$N,N,N',N'$-tetramethyl-1,2-cyclopentanediamine, $N,N,N',N'$-tetramethyl-1,2-cyclohexanediamine (cis, trans or mixtures), $N,N,N',N'$-tetramethyl-o-phenylenediamine, 4-ethyl-$N,N,N',N'$-tetramethyl-o-phenylenediamine, $N,N,N'',N''$-tetramethyl-N'-phenyl diethylene-triamine, $N,N,N',N'$-tetramethyl-1,2-ethanediamine, $N,N,N',N'$-tetramethyl-1,3-propanediamine, $N,N,N',N'',N''$-pentamethyl-diethylenetriamine, $N,N,N',N'$-tetramethyl-1,2-propanediamine, $N,N'$-dimethyl-$N,N'$-diethyl-1,2-ethanediamine, $N,N,N',N'$-tetramethyl-1-cyclohexyl-1,2-ethanediamine, $N,N,N',N'$-tetramethyl-2,3-butanediamine, $N,N,N',N'$-tetramethyl-1,4-butanediamine, $N,N,N',N'',N''',N'''$-hexamethyl triethylenetetramine, $N,N,N',N'',N''',N'''',N''''',N'''''$-octamethyl pentaethylenehexamine, beta-(dimethylamino-ethyl methyl ether, beta-diethylaminoethyl ethyl ether, bis-($\beta$-dimethylaminoethyl) ether, beta-(dimethylamino)-ethyl ethyl ether, gamma-(dimethylamino)-propyl methyl ether, ortho-dimethylamino anisole; 1,2-dipyrrolidylethane, trans-1,2-dipyrrolidyl cyclohexane, 1,2-dipiperidylethane, 1,3-dipyrrolidylpropane, 1,2-dipyrrolidylpropane, 2,2-dimethyl-1,3-dipyrrolidylpropane, 1,1,1-tris-(pyrrolidylmethyl)-ethane, $N,N'$-dipropyl-9,9-di-methylbispidin, etc.

Particularly preferred, since they generally give rise to hydrocarbon-soluble complexes and are more stable to decomposition, are the tertiary polyamines (i.e. all of the heteroatoms are tertiary nitrogen atoms) containing at least 5 carbon atoms and at least 2 tertiary nitrogen atoms. Particularly preferred species of the chelating tertiary polyamines are $N,N,N',N'$-tetramethyl-1,2-ethanediamine, $N,N,N',N'$-tetramethyl-1,3-propanediamine, $N,N,N',N'$-tetramethyl-1,2-cyclohexane-diamine (cis, trans or mixtures), $N,N,N',N'',N''$-pentamethyl diethylenetriamine, $N,N,N',N'',N''',N'''$-hexamethyl triethylenetetramine, tris-($\beta$-dimethylaminoethyl)amine and higher alkyl derivatives thereof such as the corresponding tris-($\beta$-diethylaminoethyl)amine, dipyrrolidylethane, etc.

The chelate of the lithium compound may be readily prepared by mixing the selected lithium compound (having the requisite maximum lattice energy) with the selected chelating agent in the absence of solvent. Such mixing may also be accomplished in the presence of inert hydrocarbons, e.g. $C_4$-$C_{20}$ alkanes (e.g. pentane, heptane, hexadecane); $C_6$-$C_{20}$ aromatics (e.g. benzene, toluene, xylene, dibutylnaphthalene); halogenated aromatics (e.g. chlorobenzene, dichlorobenzene, hexafluorobenzene); heterocyclic compounds (e.g. pyridine, pyrrole, furan, thiophene, sulfolane, borazole); or mixtures thereof. Preferred solvents include the aromatics, halogenated aromatics and saturated hydrocarbons.

The amount of the diluent is not critical and amounts in the range of 0 to 99.9 wt. %, based on the chelated lithium compound may be conveniently employed. Thus, the chelate can be prepared in the absence of solvents, in the form of pastes and in solutions.

In those situations where the lithium compound of choice is not solubilized by the admixture of the chelating agent and solvent, the chelate may be formed by mixing the lithium compound (which is preferably in finely divided form) with the chelating agent of choice in stoichiometric amounts, or preferably, with excess chelating agent.

Another method for preparing the chelate involves anion exchange. In this method, the chelating agent of choice is mixed with lithium compound (in which the anion is not the desired anion) by one of the methods described above. Thereafter the resultant chelate is subjected to anion exchange in the presence of a metal salt (or other well known techniques such as anion exchange resins) containing the anion of choice; alternatively, all components may be mixed simultaneously and both complexation and metathesis occurs in situ.

Another method for preparing the chelate is analogous to the preceding method except that here the anion is one of choice, but the chelating agent is not one of choice. After preparing the non-preferred chelate by one of the above methods, the non-preferred chelating agent moiety is exchanged for the preferred chelating agent moiety by mixing the chelate (utilizing one of the former methods) with the desired chelating agent and thereafter recovering the desired chelate.

Regardless of the method employed the preparation of the chelate is preferably carried out under anhydrous conditions, although this is not always necessary in some applications, such as separations.

The chelate may be readily prepared at temperatures of about −50°C. to about 200°C.; preferably 0 to 100°C.; the latter temperature range is preferred because of convenience and also since higher temperatures favor dissociation of the less stable chelates. In general, from 0.25 to 50, preferably 0.5 –10 moles of chelating agent per mole of lithium compound is employed; the chelating agent may be employed as a solvent. However, it should be understood that the amount of chelating agent employed may influence the structure of the resultant chelate. Thus, it has been found possible to prepare chelates of the following types:

1. Two moles of lithium compound to one mole of chelating agent such as (LiBr)$_2$.hexamethyltriethylenetetramine.

2. One mole of lithium compound to one mole of chelating agent, such as LiBr.pentamethyldiethylenetriamine, LiI.tetramethylethylenediamine.

3. One mole of lithium compound to two moles of chelating agent, such as LiAlH$_4$.2(tetramethylethylenediamine), LiAlH$_4$.2(tetramethylmethanediamine), LiBr.2(tetramethylethylenediamine).

Of course, the minimum amount of chelating agent should be that stoichiometric amount required to produce the desired type of chelate (where more than one type of chelate is possible from a particular lithium compound and a particular chelating agent). Where only one type of chelate can be formed or where one is not concerned with the particular type of chelate to be formed (assuming more than one type is possible), it is often desirable to employ amounts of chelating agent in excess of the stoichiometric amount.

Although we do not wish to be bound by the following theoretical structure, it is believed that the 1:1 chelate made using a tridentate chelating agent has a structure of the type represented by lithium and N,N,N′,N″,N″-pentamethyldiethylenetriamine:

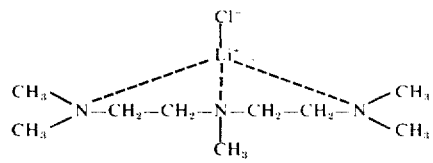

Regardless of the number of functional groups in the chelating agent, the number of functional groups solvating the lithium at one time will never be greater than four and will usually be three. Of course, the bidentate chelating agents can have only two functional groups solvating the lithium.

One of the uses of the chelates of this invention is the separation and purification of the chelating agents. Thus, chelating agents may be separated and/or purified from isomeric and/or homologous non-chelating Lewis bases or other materials. The chelating agents may be purified by complexing therewith with one of the inorganic lithium salts mentioned above and the chelating agent (and the inorganic lithium salt) may then be recovered in a pure form by destabilization of the chelate which is readily accomplished by addition of polar solvents to the complex (e.g. addition of water, ethylene glycol, methanol etc.); addition of aqueous or anhydrous acids or bases (e.g. hydrochloric acid, sulfuric acid, acetic acid, lithium hydroxide, sodium hydroxide, ammonium hydroxide, potassium hydroxide, etc.) or by heating at a temperature in the range of about 30° to 250°C. For example, this technique has not only been successful in the purification of chelating agents from their crude preparations, but it can also make possible such difficult separations as between cis and trans isomers.

The purification and/or separation processes described above may, of course, be advantageously utilized with column and counter flow techniques, i.e. the inorganic lithium salt (complexed or uncomplexed) may be contacted with a countercurrent flow of a hydrocarbon solution of the chelating complexing agent sought to be purified and the resultant complex is then subjected to destabilization to recover the desired chelating complexing agent in a pure state.

By analogy, the chelating agents may be used to purify salt mixtures and indeed to synthesize desired lithium salts. Thus, the desired lithium salt may be selectively separated in a pure state from a mixture of metal salts by contacting the mixture (simple contact, column contact and counterflow contact would be suitable) with a complexing agent and thereafter destabilizing the resultant complex as described above to recover the anhydrous pure lithium salt; the complexing agent may then be recycled for further use in purification of lithium salts. Where the anion of the lithium salt is not the desired anion, the anion of the pure complexed lithium salt may be replaced for the desired anion by anionic exchange and the resultant complex is then destabilized to recover the desired lithium salt in a pure state.

The chelating agents of this invention are also useful in separating lithium salts from each other, present as solid (or molten) mixtures or aqueous solutions, by choosing the proper chelating agent. This is an extremely useful property of these chelating agents for there is no known prior art method for achieving such facile separations.

It has been discovered that the novel chelates of this invention, particularly when dissolved in an aromatic hydrocarbon solvent, afford highly conducting systems. For example, the complex of lithium aluminum hydride with N,N,N',N'', N''-pentamethyldiethylenetriamine, when dissolved in benzene (2 molar), results in a solution having a conductivity of about $3 \times 10^{-3}$ ohm/cm.

The high conductivity of the aromatic hydrocarbon solutions of the novel complexes renders these materials extremely useful for electrochemical reactions (e.g. dimerization of anions such as $NH_2^-$ to prepare hydrazine), as supporting electrolytes and as electrolytes in storage batteries. For example, a secondary battery may be prepared using electrodes such as platinum enclosed in a container which is insoluble in the hydrocarbon solution and utilizing the solution as charge transfer liquid. Alternatively, the battery may be made in the form of a dry cell wherein one electrode, e.g. the anode, serves as the container and the other electrode is centrally spaced from the container. Porous solution-permeable separators may be placed within the electrodes. Primary batteries may also be made using these systems in which one electrode is lithium metal or an alloy. The use of these novel complexes as electrolytes in batteries is disclosed and claimed in application Ser. No. 100,813, filed Dec. 22, 1970, entitled "Electric Battery Using Complex Inorganic Lithium Salts and Charge Transfer Agent" and owned by the same assignee.

The complexed inorganic lithium salts of this invention have also been found to be extremely useful for electrochemical purposes in a solvent-free state. It is well known that molten alkali metal salts, such as lithium iodide in the molten state, are useful as electrical conductors. However, the use of such molten salts entails special equipment and procedures since they have high melting points, e.g. LiI melts at 450°C. and LiBr melts at 547°C. However, this disadvantage can be readily overcome by complexing the lithium salt with a complexing agent such as N,N,N',N'',N'''-pentamethyl-diethylenetriamine (PMDT). Crystalline LiI.PMDT complex starts to melt at about 84°C. and is completely molten at about 110°C. At 110°C., PMDT.LiBr is molten and has a conductivity of $5.2 \times 10^{-4}$ (ohm-cm)$^{-1}$. Some lithium salts, such as lithium aluminum hydride, decompose below their melting points but complexation can extend their utility. For example, $LiAlH_4$ decomposes at 110–125°C., whereas $PMDB.LiAlH_4$ melts without decomposition at 150–155°C. and can be sublimed at 125°C./0.5 mm. When complexed by HMTT, $LiAlH_4$ is stable to over 200°C.

Chelates of metal hydrides (e.g. $LiAlH_4$, $LiBH_4$, $LiAlH_3OR$, $LiAlH_2X_2$, etc.) have been found to be superior to the uncomplexed form as reducing agents. The chelate of $LiAlH_4$ and N,N,N',N'',N''-pentamethyl diethylenetriamine (PMDT) is very reactive and effective in carbonyl reduction. For example, in attempting to prepare 1,2-bis-(hydroxymethyl)cyclohexane from phthalic acid, the relatively cheap intermediate, hexahydrophthalic anhydride, was reduced to the corresponding dihydroxy compound with the conventional $LiAlH_4$-in-ether only with great difficulty and with relatively poor yield. It was therefore necessary to first hydrogenate diethyl phthalate to the corresponding hexahydro ester and thereafter reduce this ester to the dihydroxy compound. However, by using the $LiAlH_4$. PMDT chelate in benzene, the cheap hexahydrophthalic anhydride was reduced to the dihydroxy compound with an 80% yield of 96% pure material thereby saving costs of raw materials and one process step. The chelated metal hydrides are also very useful in reducing esters, ketones, aldehydes, imines, oximes, hydrazones, amides, sulfoxides, nitriles, isonitriles, alkyl sulfones (which are generally not reduced by the uncomplexed metal hydrides in ether) nitro compounds, carboxylic acids, anhydrides, α,β-unsaturated carboxyls, or other inorganic compounds, etc.

Chelation of lithium aluminum hydride and lithium borohydride also provides a new process for separating and purifying these types of compounds from their extensive impurities in commercial products. The process comprises the following steps: (a) contacting the impure complex hydride with a chelating agent, selected from the group tertiary polyamines and tertiary aminoethers, in the presence of a solvent for the chelate, and (b) separating the soluble chelated complex hydride from the insoluble impurities. It is preferred to use the pure chelate solution directly as prepared, but the pure chelates may be isolated as crystalline complexes or, in some cases, dissociated to recover the pure complex hydride separately from the chelating agent.

Suitable solvents for the chelates include aromatic hydrocarbons, pyridine, monohalogenated benzenes, alkylated benzenes, N,N-dialkylanilines and mixtures thereof including mixtures with minor amounts of saturated hydrocarbon solvents. Saturated hydrocarbon solvents may be used in a few instances, but they are generally not satisfactory. Most preferred solvents are aromatic hydrocarbons and their lower alkyl derivatives, especially benzene.

The chelated lithium compounds may be utilized in addition reactions:

As a outgrowth of this invention, it has been found possible to prepare novel chelated lithio radical anions.

These novel lithio radical anions may be prepared by two methods. In the first method, a lithium dispersion and a chelating agent are admixed with an aromatic or heterocyclic aromatic compound whose reduction potential is greater than that of biphenyl (i.e., greater than −2.70 volts in a more positive sense vs. a saturated calomel electrode and therefore will accept an electron more readily than biphenyl) (e.g. naphthalene, anthracene, biphenyl, azulene, pyracene, pyrazine benzofuran, benzo[B]thiophene, 4,4'-bipyridyl, cyano and nitrosubstituted benzenes, pyridazine, perinaphthalene, pyrene, phenanthrene, indene, isoindene, isobenzofuran, quinoline, isoquinoline, cinnoline, naphthyridine, pyrido [3,4-b] pyridine, anthranil, xanthene, acridine, dibenzothiophene, dibenzofuran, triphenylene, chrysene, 1,2-dibenzopyrene, 1,2,5,6-dibenzanthracene, coronene, fluoroanthene, acenaphthylene, tetracene, dibiphenylene-ethane, [2,2]paracyclophane, etc. as well as alkyl, cycloalkyl, cyano and nitro derivatives thereof). Depending on the particular aromatic compound of choice, a complexed mono- or di-lithio radical anion is formed; the general structure of such an anion is as follows:

[Chelating Agent.Li]⊕ |Ar|⊖

The second method involves the admixture of lithium metal and a chelating agent containing an aromatic nucleus; this chelating agent may be used as is or dissolved in a hydrocarbon. By this method, novel lithio radical anions having the following general structures may be prepared:

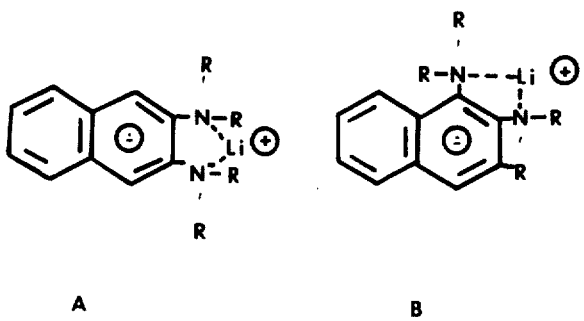

A      B

In the general formulas above, the rings may contain substituents and R is a hydrocarbon (e.g. alkyl) radical of 1 to 20 carbon atoms, preferably a $C_1$ to $C_4$ alkyl radical. It should also be understood that the multi-ring analogs (anthracene, phenanthrene, etc.) and heterocyclic aromatics, such as quinoline, as well as the alkaryl or aralkyl analogs of these chelating aromatic-tert.-diamines may be used.

The novel complexed lithio radical anions are useful as catalysts, as electrochemical media, in batteries, as reducing agents, additives and in syntheses. This invention is illustrated by the following examples:

EXAMPLE 1

To 30 ml of a 1 molar solution of pentamethyldiethylenetriamine.LiAlH$_4$(PMDT.LiAlH$_4$) in benzene was added dropwise 1.38 g (30 mmoles) of absolute ethanol in benzene. The reaction mixture was filtered removing 0.42 g of solid and the filtrate was allowed to evaporate under a nitrogen atmosphere and crystals grew. These were recovered and analyzed; theory for PMDT.LiAlH$_3$OC$_2$H$_5$; C, 51.74%; H, 12.24%; N, 16.46%. Found C, 50.85%; H, 10.72%; N, 16.63%. The NMR spectrum of the product in benzene was also consistent with that expected for PMDT.LiAlH$_3$OC$_2$H$_5$.

EXAMPLE 2

To a solution of 3.1 g (20 mmoles) of tetramethylethylenediamine.LiAlH$_4$(TMED.LiAlH$_4$) in 100 ml of benzene was added a solution of 4.61 g (20 mmoles) of tris-(β-di-methylaminoethyl) amine (iso-HMTT) in 20 ml of benzene with stirring. The mixture was filtered and the residue was dried, wt. 3.36 g. A portion of the product was recrystallized from benzene and analyzed: theory for iso-HMTT.LiAlH$_4$ C, 53.71%; H, 12.77%; N, 20.88%. Found C, 52.26%; H, 12.84%, N, 21.29%.

EXAMPLE 3

To 10 mmoles of PMDT.LiAlH$_4$ in 40 ml of benzene was added 2.93 g (40 mmoles) of diethylamine in 40 ml of benzene. The reaction mixture was stirred 3 days, concentrated, diluted with heptane and allowed to stand under a nitrogen atmosphere whereupon rod-like crystals deposited. The latter were isolated by filtration and dried. The NMR spectrum of the product in benzene showed a ratio of three dimethylamino groups to one PMDT and when water was added to the benzene solution H$_2$ gas was evolved. Thus the product was PMDT.LiAlH [(N(C$_2$H$_5$)$_2$]$_3$. Analysis: theory for PMDT.LiAlH[N(C$_2$H$_5$)$_2$]$_3$ C, 59.41%; H, 12.82%; N, 19.79%. Found C, 58.54%; H, 12.53% N, 19.05%.

EXAMPLE 4

To 16.8 mmoles of PMDT.LiCl in 20 ml of benzene was added a solution of 1.92 g (16.8 mmoles) of Al(C$_2$H$_5$)$_3$ in 20 ml of benzene. NMR analysis of the solution showed that the product was PMDT.LiAlCl(C$_2$H$_5$)$_3$.

EXAMPLE 5

To a solution of 2.60 g (10 mmole) PMDT.LiBr in 50 ml of benzene was added 10 ml of a 1 molar solution of Al(n-C$_3$H$_7$)$_3$ in heptane. NMR analysis of the solution showed that the product was PMDT.LiAlBr(n-C$_3$H$_7$)$_3$.

EXAMPLE 6

To 15 mmoles of iso-HMTT.LiN(CH$_3$)$_2$ in 75 ml of benzene was added 15 ml of a 1 molar solution of Al(n-C$_3$H$_7$)$_3$ in heptane. The solvents were stripped from the reaction mixture and the product, wt. 6.6 g, was analyzed by NMR. The spectrum was consistent with that expected for iso-HMTT. LiAl(n-C$_3$H$_7$)$_3$N(CH$_3$)$_2$.

EXAMPLE 7

Combination of iso-HMTT.LiN(CH$_3$)$_2$ with one equivalent of Al(C$_2$H$_5$)$_2$N(C$_2$H$_5$)$_2$ as described in Example 6 gave iso-HMTT. LiAl(C$_2$H$_5$)$_2$N(CH$_3$)$_2$N(C$_2$H$_5$)$_2$ by NMR Analysis.

EXAMPLE 8

Set forth in Table I are the thermal stabilities and benzene solubilities at room temperature of several crystalline complexes. These data indicate that the complexes have different stabilities and solubilities. Thus, lithium salts can be separated from one another and from other metal salts, and complexing agents may be separated from one another and from other materials. The purified lithium salts and complexing agents can be readily recovered by merely heating the complex alone or in solution at preferably above its decomposition temperature (the lithium salt starts to precipitate out at such temperatures); such destabilization heating may also be advantageously accomplished in the presence of a hydrocarbon which will solubilize the complexing agent, but not the complex or the lithium salt. Although quantitative recovery (by heating or other destabilization techniques) of the lithium salt and complexing agent is not possible in a single batch operation (because of equilibria of the destabilization reaction), a cyclic process can (and should) be used if quantitative recovery is desired.

TABLE I

| Lithium Salt | Complexing Agent | Decomposition Temp., °C. (at ~0.5 mm Hg) | Solubility in Benzene (molar) |
|---|---|---|---|
| LiCl | trans-TMCHD | 29 | 0.5 |

TABLE I -continued

| Lithium Salt | Complexing Agent | Decomposition Temp., °C (at ~0.5 mm Hg) | Solubility in Benzene (molar) |
|---|---|---|---|
| LiBr | trans-TMCHD | 125 | 0.8 |
| LiI | trans-TMCHD | 203 | 0.3 |
| LiBr | cis-TMCHD | 80 | ~0.1 |
| LiI | TM-o-PD | 97 | 0.4 |
| LiBr | TMED | 50–100 | 1.6 |
| LiNO₃ | TMED | — | 0.3 |
| LiAlH₄ | TMED | 125 (at 1.3 mm)⁽ᵉ⁾ | 0.82 |
| LiBH₄ | TMED | — | 1.0 |
| LiAlH₄ | 2 TMED | —⁽ᵇ⁾ | 0.17 |
| 2 LiBr | HMTT | ~143 | ~0.1 |
| LiBr | HMTT | ~40 | ~0.3 |
| LiNO₃ | HMTT | — | >2.0⁽ʰ⁾ |
| LiBH₄ | HMTT | — | 3.0 |
| LiAlH₄ | HMTT | >200⁽ᶜ⁾ | 0.005 |
| LiBF₄ | HMTT | — | 1.3 |
| 3 LiI | HMCHT | 60 | >0.1 |
| LiAlH₄ | TM-o-PDA | — | 1.01 |
| LiCl | PMDT | 70 | 2.5 |
| LiBr | PMDT | 86⁽ᵈ⁾ | 2.5 |
| LiI | PMDT | sublimes⁽ᶠ⁾ | 2.5 |
| LiNO₃ | PMDT | — | 2.66 |
| LiBH₄ | PMDT | 75 (at 1 mm)⁽ᶠ⁾ | forms gel⁽ʲ⁾ |
| LiAlH₄ | PMDT | —⁽ᵍ⁾ | 1.8 |
| LiBF₄ | PMDT | —⁽ʰ⁾ | 0.19 |
| LiPF₆ | PMDT | — | 1.25 |
| LiB(C₆H₅)₄ | PMDT | — | 0.04 |
| LiNO₃ | iso-HMTT | — | >1.0 |
| LiCl | n-HMTP(k) | 100–105 | >2.0 |

⁽ᵃ⁾blackens above 176°C.
⁽ᵇ⁾M.P. 118–120°C.
⁽ᶜ⁾stable to 200°C.; M.P. >200°C.
⁽ᵈ⁾M.P. 92–93.5°C.
⁽ᵉ⁾M.P. 89–110°C.
⁽ᶠ⁾M.P. 74–81°C.
⁽ᵍ⁾sublimes w/o decomp. at 125°C./0.5 mm; M.P. 150–155°C.
⁽ʰ⁾M.P. 118–121°C.
⁽ⁱ⁾Solubility greater than 3 molar at 25°C.
⁽ʲ⁾HMTT.LiNO₃ is a liquid at 25°C.
⁽ᵏ⁾N,N,N',N'',N''',N'''',N''''' –heptamethyltetraethylenepentamine.

EXAMPLE 9

To 6 mmoles of PMDT.LiAlH₄ in benzene was added 3.57 g (12 mmoles) of HN(n-C₁₀H₂₁)₂. The reaction mixture was stirred overnight and the product, wt. 4.8 g, was analyzed by NMR. It was PMDT.LiAlH₂[N(n-C₁₀H₂₁)₂]₂.

EXAMPLE 10

To a benzene solution of 8 mmoles of PMDT. LiAlH₃OC₂H₅ was added 2.98 g (10 mmoles) of HN(C₁₀H₂₁)₂ and the reaction mixture was stirred overnight. The reaction mixture was concentrated and filtered removing about 0.5 g of white solid. The filtrate was analyzed by NMR and the product was PMDT.LiAlH₂OC₂H₅N(C₁₀H₂₁)₂.

EXAMPLE 11

To 25 mmoles of PMDT.LiAlH₃N(C₂H₅)₂ in benzene was added 25 mmoles of absolute C₂H₅OH. The product was PMDT. AlH₂OC₂H₅N(C₂H₅)₂ by NMR analysis.

EXAMPLE 12

To 15 mmoles of PMDT.LiAlH₄ in benzene was added 2.19 g (15 mmoles) of HSC₈H₁₇ in 30 ml of benzene. The reaction mixture was stirred overnight, concentrated and analyzed by NMR. The product was PMDT.LiAlH₃SC₈H₁₇, wt. 5.4 g.

EXAMPLE 13

Lithium aluminum hydrate, 0.37 g. (19 mmole) was mixed with 1.44 g. (10 mmole) of N,N,N',N'-tetramethyl-1,4-butanediamine (TMBD). The resulting paste was stirred for 18 hours then diluted with 6 ml. benzene and filtered. The insoluble complex weighed 1.40 g. and upon evaporation of 2 g. of the filtrate, an additional 0.05 g. of white solid was obtained, thus indicating that LiAlH₄.TMBD has some solubility in benzene.

LiAlH₄, 3.80 g. (100 mmole) was dispersed in 50 ml. of benzene and 11.62 g. (100 mmole) of TMED were added. The mixture was diluted to 100 ml. of benzene, stirred at room temperature for hours and filtered. A grey residue of 0.22 g. (5.8% of the starting LiAlH₄) was removed and the clear, colorless filtrate was allowed to evaporate under nitrogen. A white crystalline solid was isolated by filtration and the mother liquor was allowed to evaporate further and a second and third crop of crystals were isolated. A total quantity of 9.0 g. of 1:1 complex of LiAlH₄ and TMED was obtained.

To a 25 ml. portion of 0.75 molar solution of LiAlH₄.TMED in benzene was added dropwise an additional 2.18 g. (18.75 mmole) of TMED with stirring. A white precipitate (4.28 g.) was isolated by filtration of the mixture. This solid, upon analysis, indicated that a 1:2 complex of LiAlH₄ and TMED was formed. Thus, LiAlH₄ and TMED can form two distinct compositions of matter: LiAlH₄.TMED and LiAlH₄.2 TMED.

Using the procedure described above, the crystalline complex LiAlH₄.PMDT and the crystalline complex LiAlH₄.HMTT were prepared. The former was found to be so highly soluble in pure benzene that it was found that as a preferred procedure for obtaining the crystalline complex LiAlH₄.PMDT, it was desirable to add heptane to the solution (whereupon it split into two liquid phases) and allow crystals to grow from the resultant two phase mixture by solvent evaporation. The crystalline complex LiAlH₄.HMTT was prepared by complexing agent exchange from both LiAlH₄.PMDT and LiAlH₄.TMED by addition of HMTT to benzene solutions of the complexes. LiAlH₄.HMTT precipitated in nearly quantitative yield.

LiBH₄.PMDT was prepared by the method described for the preparation of LiAlH₄.PMDT and LiBH₄.HMTT was prepared from LiBH₄ and HMTT. The complexing agent exchange was not used to prepare the latter complex since LiBH₄.HMTT is very soluble in benzene in contrast to LiAlH₄.HMTT.

The results of this example are summarized in Table II below.

TABLE II

| Lithium Salt, g. (moles) | Complexing Agent g. (moles) | Isolated Complex, g. | Found | | | | Theory | | | |
|---|---|---|---|---|---|---|---|---|---|---|
| LiAlH₄, 3.8 g. (100 mmole) | TMED, 11.62 g. (100 mmole) | 9.0 g. | C: 46.66 | N: 18.56 | C: 46.75 | N: 18.17 | H: 13.42 | Al: 17.48 | H: 13.08 | Al: 17.5 |
| LiAlH₄, 0.72 g. (19 mmole) | 2 TMED, 4.36 g. (38 mmole) | 4.28 g. | C: 53.43 | N: 20.67 | C: 53.31 | N: 20.72 | H: 13.34 | Al: 9.98 | H: 13.42 | Al: 9.98 |
| LiAlH₄, 2.85 g. | PMDT, 13.01 g. | 6.5 g. | C: 49.85 | N: 19.42 | C: 51.17 | N: 19.89 |  |  |  |  |

TABLE II-continued

| Lithium Salt, g. (moles) | Complexing Agent g. (moles) | Isolated Complex, g. | | Found | | | | Complex Analysis | | Theory | |
|---|---|---|---|---|---|---|---|---|---|---|---|
| (75 mmole) LiAlH$_4$, 1.43 g. (37 mmole) | (75 mmole) HMTT, 8.64 g. (37 mmole) | 9.95 g. | H: C: H: | 12.41 53.18 12.57 | Al: N: Al: | 13.39 20.44 9.86 | H: C: H: | 12.88 53.70 12.77 | Al: N: Al: | 12.77 20.88 10.05 | |
| LiAlH$_4$, 1.9 g. (50 mmole) | TM-o-PD, 8.21 g. (50 mmole) | 2.9 g. | C: H: | 59.14 9.21 | N: | 12.73 | C: H: | 59.40 9.97 | N: | 13.86 | |
| LiBH$_4$, 2.18 g. (100 mmole) | PMDT, 17.5 g. (100 mmole) | 6.0 g. | C: H: | 56.03 13.95 | N: Li: | 21.44 3.75 | C: H: | 55.41 13.95 | N: Li: | 21.54 3.56 | |
| LiBH$_4$, 1.09 g. (50 mmole) | HMTT, 11.52 g. (50 mmole) | 1.8 g. | C: H: | 57.24 13.63 | N: Li: | 22.89 2.81 | C: H: | 57.15 13.59 | N: Li: | 22.22 2.75 | |
| LiBH$_4$, 0.50 g. (23 mmole) | TMED, 2.9 g. (25 mmole) | 1.7 g. | C: H: | 52.19 15.14 | N: | 19.91 | C: H: | 52.21 14.50 | N: | 20.31 | |

The infrared spectrum of lithium aluminum hydride alone in Nujol has two bands at 1775 and 1625 cm.$^{-1}$ of equal intensity for the Al-H stretch (these assignments have been verified by infrared spectra of LiAlD$_4$). This is because LiAlH$_4$ follows C$_2$V symmetry which predicts at least two Al—H stretching frequencies and indicates considerable H—Li—H interaction approaching a 3 center-2 electron bond (Figure A) resulting in a rather covalent compound. LiAlH$_4$.PMDT in Nujol has only one Al—H stretch at 1690 cm.$^{-1}$. This can only occur if the AlH$_4$ anion now follows Td symmetry selection rules which predict only one infrared active Al—H stretch. Thus, the AlH$_4$ anion in the complex is tetrahedral and the complex is more ionic as the H—Li—H interaction has been removed (Figure B). The substance is now a cation solvated contact ion pair.

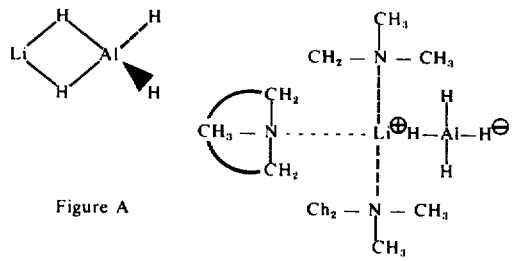

Figure A

Figure B

The significance of these findings is that in LiAlH$_4$.PMDT (and LiAlH$_4$.HMTT), the AlH$_4$ anion is fundamentally different from that of uncomplexed LiAlH$_4$. The anion is a free AlH$_4$ anion in a contact ion pair rather than part of a covalent molecule. Associated with such changes in the structure are increased reactivity, such as in reductions, and increased conductivity. The same infrared spectral changes have been found for LiBH$_4$ vs. LiBH$_4$.HMTT. Differences in the infrared spectrum of the anion of Lithium-Anion vss. Lithium-Anion.Complexing Agent are direct evidence for the complexes being distinct compositions of matter having unique properties and not solutions or mixtures of a salt and a complexing agent.

By using these techniques, impure commercial LiAlH$_4$ and LiBH$_4$ may be easily purified of associated contaminants as the latter do not pass into benzene solution in the presence of these complexing agents. Filtration of the mixture followed by evaporation of the solvent, destabilization of the complex and removal of the complexing agent would afford extremely pure LiAlH$_4$ or LiBH$_4$. Alternatively, the pure hydrides could be precipitated from solution by heating or by addition of another substance which complexes more strongly with the complexing agent than do the hydrides. Preferably, the complexes are utilized directly in the solvents in which they are prepared.

EXAMPLE 14

3.35 g. (25 mmole) of LiI was dispersed in 50 ml. of benzene and 5.88 g. (25 mmole) of N'-phenyl-N,N,N'λ',N''-tetramethyldiethylenetriamine (N'-φ-TMDT) was added with stirring and after 18 hours the mixture was filtered. The fine, white solid residue weighed 2.74 g. and the filtrate deposited colorless cyrstals when allowed to partially evaporate. The solid residue analyzed as a 1:1 chelate of N'-φ-TMDT and LiI.

In a similar manner N'-φ-TMDT.LiAlH$_4$ was prepared and the data are summarized in Table III. Therefore, the chelating agent of an inorganic lithium salt chelate may have an aryl group attached to a nitrogen atom as well as alkyl groups.

TABLE III

| Chelating Agent, g. | Salt, g. | Chelate Isolated, g. | Analysis |
|---|---|---|---|
| N'-φ-TMDT (5.88) | LiI (3.35) | 2.5 | Theory C 45.53 H 6.78 N 11.38 Found C 45.90 H 7.11 N 11.41 |
| N'-φ-TMDT (5.88) | LiAlH$_4$ | 0.5 | Theory C 61.55 H 10.62 N 15.38 Found C 61.03 H 10.80 N 15.26 |

EXAMPLE 15

0.95 g. (25 mmole) of LiAlH$_4$ was dispersed in 25 ml. of benzene and 2.55 g. (25 mmole) of tetramethylmethane diamine (TMMD) was added with stirring. After 18 hours, stirring was stopped, the reaction mixture was allowed to settle and 2 g. of the clear liquid phase was transferred to a watch glass and allowed to evaporate. A white crystalline residue, wt. 0.1 g. remained which reacted vigorously with water evolving gas.

0.95 g. (25 mmole) of LiAlH$_4$ was dispersed in 10 ml. of benzene, 5.11 g. of TMMD (50 mmole) was added, the mixture was diluted to 24 ml. and stirred for 20 hours. The reaction mixture was filtered and a gray solid residue, wt. 0.35 g., remained on the filter disc (ASTM-10-15). The clear colorless filtrate afforded white crystals upon partial evaporation which evolved hydrogen gas when hydrolyzed. Therefore, an excess of the complexing agent gives a greater amount of $LiAlH_4$ complex in solution.

The above data demonstrate that inorganic lithium salts and ditertiary amines in which both nitrogens atoms are on the same carbon atom can form complexes which may be hydrocarbon soluble.

EXAMPLE 16

To 210 ml. of 1.0 M $LiAlH_4 \cdot PMDT$ (0.21 mole in benzene) was added dropwise a solution of 45.5 g. of diethyl hexahydrophthalate. A vigorous reaction occurred and the flask was cooled to maintain the temperature at 30°–40°C. After addition, the reaction mixture (pasty) was refluxed for about 3 hours. The mixture was cooled and hydrolyzed with 10% hydrochloric acid. The benzene solution was separated and the aqueous phase was washed with three 200 ml. portions of ether. The combined benzene solution and ether extracts were washed with water and sodium bicarbonate solution and dried over anhydrous $Na_2SO_4$.

The solution was filtered and ether-benzene was stripped off. The residue was simply distilled under reduced pressure. A product was collected (b.p. 123–125°C. at 0.5 mm, wt. 17.0 g.) which solidified on standing. Residue = 3.2 g.

Infra-red analysis showed a broad OH band at about 3300 $cm.^{-1}$ and no carbonyl band at 1740 $cm.^{-1}$. G.C. analysis showed product to be 93% pure trans-1,2-cyclohexanedimethanol.

A number of additional runs were made using benzene solutions of PMDT in various mole ratios to $LiAlH_4$, TMED as the chelating agent and hexahydrophthalic anhydride instead of diethyl hexahydrophthalate as the substance to be reduced. The data from these experiments are summarized in Table IV. Reaction times varied from two to 18 hours, but even a reaction time of 2 hours is probably unnecessary. Reduction appeared to be complete within minutes.

In contrast to the results summarized in Table IV, reduction of diethyl hexahydrophthalate or hexahydrophthalic anhydride with excess $LiAlH_4$ by conventional procedures in ether solvents gave impure glycol in very low yield only after extended reaction times.

Clearly, chelated $LiAlH_4$ in benzene is a far superior reducing agent to $LiAlH_4$ in ether solvents. Yields are higher incomplete reductions are avoided and reaction times are an order of magnitude or more shorter.

EXAMPLE 17

To 15 mmoles of $PMDT.LiAlH_4$ in 60 ml. of benzene was added 1.65 g. (15 mmoles) of $C_6H_5SH$. Vigorous gas evolution occurred and the resulting solution was allowed to evaporate under a nitrogen atmosphere until crystals deposited. The latter were recovered by filtration, wt. 2.8 g., washed with pentane, dried and analyzed.

TABLE IV

| Run | Chelating Agent and Mole Ratio to $LiAlH_4$ | Reaction Time, hrs. | Chel.$LiAlH_4$ Preformed | Compound Reduced g. (moles) | $LiAlH_4$, g. | Yield of Distilled Product, % | % Purity of Product |
|---|---|---|---|---|---|---|---|
| 1 | PMDT 1:1 | 3 | Yes | diester 45.5 (0.2) | 8.0 | 59 | 93 |
| 2 | PMDT 1:1 | 3 | Yes | anhydride 30.8 (0.2) | 8.0 | 28 | 93 |
| 3 | PMDT 0.25:1 | 4 | No | anhydride 77 (0.5) | 21.8 | 30 | 91 |
| 4 | PMDT 0.5:1 | 4 | No | anhydride 77 (0.5) | 21.8 | 34 | 90 |
| 5 | PMDT 0.75:1 | 4 | No | anhydride 77 (0.5) | 21.8 | 38 | 91 |
| 6 | PMDT 1:1 | 4 | No | anhydride 77 (0.5) | 21.8 | 29 | 88 |
| 7 | TMED 1:1 | 4 | No | anhydride 77 (0.5) | 21.8 | 39 | 90 |
| 8 | TMED 1:1 | 2 | No | diester 2215 (9.7) | 424.2 | 81 | 96 |
| 9 | none[a] | 24 | — | diester 2652 (11.6) | 445 | 30 | 89[b] |

[a] solvent diethyl ether rather than benzene
[b] runs 1–8 distilled in simple one-plate column, run 9 distilled in 45-plate spinning band column the NMR spectrum of the material in $C_6D_6$ was consistant with that expected for $PMDT.LiAlH_3SC_6H_5$ as was the elemental analysis: theory C, 56.40%; H, 9.78%; N, 13.16%. Found C, 54.97%; H, 9.56%; N, 13.13%.

EXAMPLE 18

To 15 mmoles of PMDT • $LiAlH_4$ in 60 ml. of benzene was added 1.10g. (15 mmoles) of $HN(C_2H_5)_2$. When gas evolution ceased 1.65 g. (15 mmoles) of $HSC_6H_5$ was also added. The clear colorless solution was concentrated under vacuum at room temperature affording a clear liquid residue, wt. 5.9 g., which was analyzed by NMR and found to be PMDT • $LiAlH_2N(C_2H_5)_2SC_6H_5$.

EXAMPLE 19

Trans-TMCHD • $LiAl(CH_3)_4$ was prepared from trans-TMCHD and $LiAl(CH_3)_4$ using a 1:1 molar ratio in benzene solvent.

EXAMPLE 20

Lithium bromide, 0.43 g. (0.005 mole) was dispersed in 5 ml. benzene and 0.98 g. (0.005 mole) of 1,2-bis-(piperidino)-ethane was added with stirring. After 18 hours, the solid increased substantially in volume and a fluffy white material resulted. The mixture was filtered and 1.44 g. of a slightly wet solid complex was isolated (theory: 1.41 g.). This example illustrates the possibility of using as the complexing agent a compound in which the alkyl groups attached to the nitrogen atoms may be part of a saturated heterocycle. Analysis The ory: C 50.9%; H 8.48%; N 9.90%. Found: C 56.23%; H 8.67%; N 8.27%.

EXAMPLE 21

To 10 mmoles of sparteine in 50 ml. of benzene is added 10 mmoles of LiBH₄ with stirring. The product is sparteine • LiBH₄.

EXAMPLE 22

A stock solution was prepared by mixing 320 mg. (2.5 mmole) of sublimes naphthalene and 575 mg. (2.5 mmole) of iso-HMTT in a 50 ml. volumetric flask and diluting to the mark with dry benzene. One-half of this solution was transferred under nitrogen to a 100 ml. flask which contained 0.64 g. of lithium shavings. After 1 hour a dark green solution of the radical ion chelate was obtained. After ca. 45 hours a 5 ml. aliquot of this reaction mixture was diluted to 50 ml. and about 1 ml. of this solution was placed in a dry 4 mm O.D. pyrex glass sample tube for esr analysis. The esr spectrum confirmed the presence of the paramagnetic species iso-HMTT • Li⁺C₁₀H₈⁻̇.

EXAMPLE 23

Naphthalene (1.95 g., 15 mmole) 1,2-dipyrrolidylethane (DPYE) (2.52 g., 15 mmole), lithium dispersion (0.075 g.) and 15 ml. of benzene were combined and stirred. The precipitate which formed was isolated by filtration (2.24 g.); the filtrate was concentrated to give 1.3 g. additional product. The chelated radical anion was DPYE • Li⁺C₁₀H₈⁻̇.

EXAMPLE 24

1,2-Dipyrrolidylethane (3.36 g., 20 mmole), lithium bromide (1.74 g., 20 mmole), and 75 ml. of benzene were combined and stirred overnight. The mixture was filtered and the residue was vacuum dried for 1 hour to give 3.0 g. of white solid complex. Elemental analysis (C, H, and N) suggested a composition containing a 1 to 1.5 ratio of DPYE to LiBr.

EXAMPLE 25

Terphenyl (3.465 g., 15 mmole), PMDT (2.595 g., 15 mmole), lithium dispersion (0.075 g.) and 20 ml. of benzene were combined. After stirring overnight the thick green suspension was filtered to give 4.7 g. of the green solid radical anion PMDT.Li⁺[Ω-Ω-Ω]⁻̇.

EXAMPLE 26

A 1.29 g. (5 mmoles) portion of Al(C₆H₅)₃ was mixed with 100 ml. of benzene and the mixture was heated to 70°C. with stirring. To the clear solution was added 1.30 g. (5 mmoles) of PMDT.LiBr in 65 ml. of benzene and the mixture was stirred at 70°C. for 2 hours, cooled to room temperature and filtered, removing 0.08 g. of solid. The filtrate was evaporated under reduced pressure and the product, wt. 2.6 g., was analyzed by NMR in C₆D₆ and was found to be PMDT.LiAl(C₆H₅)₃Br.

While the above examples illustrate the invention in great detail, it should be understood that the present invention in its broadest aspects is not necessarily limited to the specific materials, conditions and procedures shown therein. The present invention is limited only by the claims which will follow.

What is claimed is:

1. A complex comprising: (a) a lithium hydrido aluminate having a lattice energy less than 210 kilocalories per mole at 18°C and (b) a monomeric or polymeric polyfunctional chelating tertiary hydrocarbyl amine containing at least 2 nitrogen atoms.

2. A complex according to claim 1 wherein the amines are chelating polyfunctional Lewis bases, said bases being ones selected from the group consisting of tris-(2-C₁-C₄ dialkylaminoethyl)-amine and those compounds having the formulas:

(I) 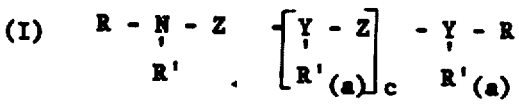

(II) 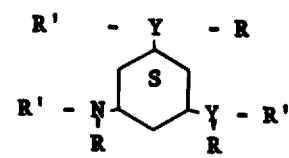

wherein c is an integer of 0 to 10,000 inclusive; Y is one selected from the group consisting of N and O; a is an integer equal to 0 or 1 depending on whether Y is N or O; R is the same of different C₁-C₄ alkyl radical; R' is the same or different C₁-C₄ alkyl radical or C₆-C₁₀ aryl or aralkyl radical; and Z is a nonreactive radical selected from the group consisting of:

1. C₄-C₁₀ cycloaliphatic or aromatic radicals and their lower alkyl derivatives wherein said radicals are attached to the N atoms in Formula I at 1,2 positions on the aromatic rings or 1,2 or 1,3 positions on the cycloaliphatic rings; and
2. 1 to 4 methylenic radicals, wherein each methylenic radical contains 0 to 2 monovalent hydrocarbon radicals of 1 to 6 carbon atoms.

3. A complex according to claim 1 which is pentamethyldiethylenetriamine   LiAlH₃OC₂H₅.

4. A complex according to claim 1 which is tris-(B-dimethylaminoethyl)amine   LiAlH₄.

5. A complex according to claim 1 which is pentamethyldiethylenetriamine   LiAlH[N(C₂H₅)₂]₃.

6. A complex according to claim 1 which is pentamethyldiethylenetriamine   LiAlCl(C₂H₅)₃.

7. A complex according to claim 1 which is pentamethyldiethylenetriamine   LiAlH₂N(C₂H₅)₂SC₆H₅.

8. A complex according to claim 1 which is a trans-tetramethylcyclohexanediamine   LiAlH₄.

* * * * *

UNITED STATES PATENT OFFICE
CERTIFICATE OF CORRECTION

Patent No. 3,933,879   Dated January 20, 1976

Inventor(s) Arthur W. Langer, Jr. Thomas A. Whitney

It is certified that error appears in the above-identified patent and that said Letters Patent are hereby corrected as shown below:

Column 7, line 55, cancel "PMDB·LiAlH$_4$" and insert
-- PMDT·LiAlH$_4$ -- therefor.
Column 14, lines 33-34, cancel "N'-phenyl-N,N,N'λ',N" " and insert -- N'-phenyl-N,N,N",N" -- therefor.
Column 17, line 11, "sublimes" should read -- sublimed --.
Column 17, line 48, cancel "[Ω-Ω-Ω]$^±$ " and insert
-- [ø-ø-ø]$^±$ -- therefor.

Signed and Sealed this

Seventh Day of September 1976

[SEAL]

Attest:

RUTH C. MASON
*Attesting Officer*

C. MARSHALL DANN
*Commissioner of Patents and Trademarks*